United States Patent [19]
MacLeod

[11] Patent Number: 6,066,625
[45] Date of Patent: May 23, 2000

[54] OPTIMIZED ANTISENSE OLIGONUCLEOTIDES COMPLEMENTARY TO DNA METHYLTRANSFERASE SEQUENCES

[75] Inventor: Robert A. MacLeod, Westmount, Canada

[73] Assignee: Methylgene, Inc., St. Laurent, Canada

[21] Appl. No.: 09/018,034

[22] Filed: Feb. 3, 1998

[51] Int. Cl.[7] .............................. A61K 48/00; C12N 9/00; C12N 15/85; C12N 15/11; C07H 21/04

[52] U.S. Cl. .......................... 514/44; 435/183; 435/193; 435/325; 435/366; 435/371; 435/375; 536/23.1; 536/24.5

[58] Field of Search ............................... 435/6, 69.1, 91.1, 435/440, 183, 193, 325, 366, 371, 375, 320.1; 536/23.1, 24.3, 24.31, 24.33, 24.5; 514/44

[56] References Cited

U.S. PATENT DOCUMENTS

| | | |
|---|---|---|
| 5,030,557 | 7/1991 | Hogan et al. ............................. 435/6 |
| 5,578,716 | 11/1996 | Szyf et al. . |
| 5,652,355 | 7/1997 | Metelev et al. . |

OTHER PUBLICATIONS

Gura, T. Science, vol. 278, No. 7, Nov. 1997, pp. 1041–1042, Nov. 1997.
Qian, M. et al. J. Pharmacology and Experimental Therapeutics, vol. 282, No. 2, Aug. 1997, pp. 663–670, Aug. 1997.
Szyf et al. (1996) *Pharmacol. Ther.* 70:1–37.
MacLeod et al. (1993) *Mol. Biol. Cel.* 4:193A.
MacLeod et al. (1995) *J. Biol. Chem.* 270:8037–8043.
Shibahara et al. (1989) *Nucleic Acids Research* 17:239–252.
Holt et al. (1998) *Molecular & Cell Biology* 8:963–973.
Helene et al. (1985) *Biochemie* 67:777–783.
Cooney (1988) *Science* 241:456–459.
Tidd et al. (1990) *Anticancer Res.* 10:1167–1182.
Weiss (1991) *Science News* 139:108–109.
James (1991) *Antiviral Chemistry & Chemotherapy* 2:191–214.
Marshall et al. (1993) *Science* 259:1564–1570.
Westermann et al. (1989) *Biomed. Biochim. Acta.* 48:85–93.
Tsang et al. (1994) *Cancer Gene Therapy* 1:65–71.
Stein et al. (1993) *Science* 261:1004–1012.
Kastner et al. (1990) *EMBO J.* 9:1603–1614.
Verspleren et al. (1987) *Gene* 61:307–315.
Uhlman et al. (1990) *Chemical Reviews* 90:543–584.
Shibahara et al. (1987) *Nucleic Acids Research* 15:4403–4415.
Wickstrom et al. (1991) *FASEB J.* 5:A1443.
Sitruk–Ware et al. (1990) *Contraception* 41:221–243.
Wickstrom (1992) *TIBTECH* 10:281–287.
Tidd et al. (1989) *British J. Cancer* 60:343–350.
Quartrin et al. (1989) *Nucleic Acids Research* 17:7253–7262.
Inoue et al. (1987) *Nucleic Acids Research* 15:6131–6149.
Wickstrom (1986) *J. Biochem. Biophys. Meth.* 13:97–102.
Inoue et al. (1987) *FEBS Lett.* 215:327–330.
Quartrin et al. (1989) *Biochemistry* 28:1040–1047.
Shibahara et al. (1989) *Nucleic Acids Research* 17:239–252.
Agrawal et al (1995) *Biochemical Pharmacology* 50:571–576.
Zhang et al. (1995) *Biochemical Pharmacology* 50:545–566.
Maniatis et al. (1987) *Science* 236:1237–1245.
Peterson et al. (1993) *Annu. Rev. Genet.* 27:7–31.
Holliday (1990) *Philos. Trans. R. Soc. Lond. B. Biol. Sci.* 326:329–338.
Lock et al. (1987) *Cell* 48:39–46.
Bartolomei et al. (1993) *Genes Dev.* 7:1663–1673.
Brandeis et al. (1993) *EMBO J.* 12:3669–3677.
Szyf et al. (1995) *J. Biol. Chem.* 267:12831–12836.
Pon (1993) *Methods in Molec. Biol.* 20:465–497.
Szyf et al. (1995) *J. Biol. Chem.* 270:12690–12696.
Freedman et al. (1974) *Cell* 3:355–359.
Meyer et al. (1989) *Int. J. Cancer* 43:851–856.

*Primary Examiner*—George C. Elliott
*Assistant Examiner*—Mark L. Shibuya
*Attorney, Agent, or Firm*—Hale and Dorr LLP

[57] ABSTRACT

The invention provides optimized antisense oligonucleotides complementary to the DNA methyltransferase gene or its RNA transcript. The invention further provides methods for using such antisense oligonucleotides as analytical and diagnostic tools, as potentiators of transgenic plant and animal studies and gene therapy approaches, and as potential therapeutic agents.

5 Claims, 4 Drawing Sheets

5' AUCCGAGGAGGGCUACCUGG 3'     [SEQ ID NO 1]

5' GGAGAACGGUGCUCAUGCUU 3'     [SEQ ID NO 2]

5' GUGGCCUUGGCUGACAUGAA 3'     [SEQ ID NO 3]

5' AAGCUGUUGUGUGAGGUUCG 3'     [SEQ ID NO 4]

5' UUGUGUGAGGUUCGCUUAUC 3'     [SEQ ID NO 5]

5' CAUGGUGUUUGUGGCCUUGG 3'     [SEQ ID NO 6]

5' UAGAGUGGGAAUGGCAGAUG 3'     [SEQ ID NO 7]

FIG. 1

| | |
|---|---|
| 5' CCAGGTAGCCCTCCTCGGAT 3' | [SEQ ID NO 8] |
| 5' AAGCATGAGCACCGTTCTCC 3' | [SEQ ID NO 9] |
| 5' TTCATGTCAGCCAAGGCCAC 3' | [SEQ ID NO 10] |
| 5' CGAACCTCACACAACAGCTT 3' | [SEQ ID NO 11] |
| 5' GATAAGCGAACCTCACACAA 3' | [SEQ ID NO 12] |
| 5' CCAAGGCCACAAACACCATG 3' | [SEQ ID NO 13] |
| 5' CCAGGTAGCCCTCCTCGGAU 3' | [SEQ ID NO 15] |
| 5' AAGCATGAGCACCGTTCUCC 3' | [SEQ ID NO 16] |
| 5' UUCATGTCAGCCAAGGCCAC 3' | [SEQ ID NO 17] |
| 5' CGAACCTCACACAACAGCUU 3' | [SEQ ID NO 18] |
| 5' GAUAAGCGAACCTCACACAA 3' | [SEQ ID NO 19] |
| 5' CCAAGGCCACAAACACCAUG 3' | [SEQ ID NO 20] |

FIG. 2

| Sequence | (SEQ ID NO) | IC$_{50}$ (nM)[1] | (SEQ ID NO) | IC$_{50}$ (nM)[2] |
|---|---|---|---|---|
| 5' CCAGGTAGCCCTCCTCGGAT 3' | [8] | 90 | [15] | 70 |
| 5' AAGCATGAGCACCGTTCTCC 3' | [9] | 66 | [16] | 43 |
| 5' TTCATGTCAGCCAAGGCCAC 3' | [10] | 67 | [17] | 60 |
| 5' CGAACCTCACACAACAGCTT 3' | [11] | 96 | [18] | 75 |
| 5' GATAAGGCGAACCTCACACAA 3' | [12] | 90 | [19] | 81 |
| 5' CCAAGGCCACAAACACCATG 3' | [13] | 66 | [20] | 60 |
| 5' CATCTGCCATTCCCACTCTA 3' | [14][3] | 133 | [21] | 114 |
| scrambled sequence | -- | >>250 | -- | >>250 |

[1] oligodeoxynucleoside phosphorothioate

[2] hybrid oligonucleoside phosphorothioate with four 2-O-methyl ribonucleosides at each end and deoxyribonucleotides in the middle, any thymidine within four nucleotides from either the 5' or the 3' end of the antisense oligonucleotide is substituted with a uridine in the hybrid oligonucleotides.

[3] control prior art oligonucleotide spanning translation initiation site

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:1:

AUCCGAGGAG GGCUACCUGG                                           20

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:2:

GGAGAACGGU GCUCAUGCUU                                           20

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:3:

GUGGCCUUGG CUGACAUGAA                                           20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:4:

AAGCUGUUGU GUGAGGUUCG                                                         20

(2) INFORMATION FOR SEQ ID NO:5:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:5:

UUGUGUGAGG UUCGCUUAUC                                                         20

(2) INFORMATION FOR SEQ ID NO:6:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:6:

CAUGGUGUUU GUGGCCUUGG                                                         20

(2) INFORMATION FOR SEQ ID NO:7:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:7:

UAGAGUGGGA AUGGCAGAUG                                                         20

(2) INFORMATION FOR SEQ ID NO:8:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:8:

CCAGGTAGCC CTCCTCGGAT                                                         20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid     (iii) HYPOTHETICAL: NO     (iv) ANTI-SENSE: NO     (xi) SEQUENCE DESCRIPTION: SEQ ID NO:9:

AAGCATGAGC ACCGTTCTCC        20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid     (iii) HYPOTHETICAL: NO     (iv) ANTI-SENSE: NO     (xi) SEQUENCE DESCRIPTION: SEQ ID NO:10:

TTCATGTCAG CCAAGGCCAC        20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid     (iii) HYPOTHETICAL: NO     (iv) ANTI-SENSE: NO     (xi) SEQUENCE DESCRIPTION: SEQ ID NO:11:

CGAACCTCAC ACAACAGCTT        20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid     (iii) HYPOTHETICAL: NO     (iv) ANTI-SENSE: NO     (xi) SEQUENCE DESCRIPTION: SEQ ID NO:12:

GATAAGCGAA CCTCACACAA        20

(2) INFORMATION FOR SEQ ID NO:13:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:13:

CCAAGGCCAC AAACACCATG                                                         20

(2) INFORMATION FOR SEQ ID NO:14:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:14:

CATCTGCCAT TCCCACTCTA                                                         20

(2) INFORMATION FOR SEQ ID NO:15:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:15:

CCAGGTAGCC CTCCTCGGAU                                                         20

(2) INFORMATION FOR SEQ ID NO:16:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:16:

AAGCATGAGC ACCGTTCUCC                                                         20

(2) INFORMATION FOR SEQ ID NO:17:

(i) SEQUENCE CHARACTERISTICS:
           (A) LENGTH: 20 base pairs (B) TYPE: nucleic acid
          (C) STRANDEDNESS: single
          (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:17:

UUCATGTCAG CCAAGGCCAC                                                    20

(2) INFORMATION FOR SEQ ID NO:18:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:18:

CGAACCTCAC ACAACAGCUU                                                    20

(2) INFORMATION FOR SEQ ID NO:19:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:19:

GAUAAGCGAA CCTCACACAA                                                    20

(2) INFORMATION FOR SEQ ID NO:20:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:20:

CCAAGGCCAC AAACACCAUG                                                    20

```
(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:21:

CATCTGCCAT TCCCACTCTA                                              20
```

OPTIMIZED ANTISENSE OLIGONUCLEOTIDES COMPLEMENTARY TO DNA METHYLTRANSFERASE SEQUENCES

BACKGROUND OF THE INVENTION

1. Field of the Invention

The invention relates to modulation of gene expression. In particular, the invention relates to modulation of gene expression of the gene encoding DNA methyltransferase, and to modulation of gene expression that is regulated by the enzyme DNA methyltransferase.

2. Summary of the Related Art

Modulation of gene expression has become an increasingly important approach to understanding various cellular processes and their underlying biochemical pathways. Such understanding enriches scientific knowledge and helps lead to new discoveries of how aberrancies in such pathways can lead to serious disease states. Ultimately, such discoveries can lead to the development of effective therapeutic treatments for these diseases.

One type of cellular process that is of particular interest is how the cell regulates the expression of its genes. Aberrant gene expression appears to be responsible for a wide variety of inherited genetic disorders, and has also been implicated in numerous cancers and other diseases. Regulation of gene expression is a complex process, and many aspects of this process remain to be understood. One of the mysteries of this process resides in the fact that while the genetic information is the same in all tissues that constitute a multicellular organism, the expression of functions encoded by the genome varies significantly in different tissues.

In some cases, tissue-specific transcription factors are known to play a role in this phenomenon. (See Maniatis et al., Science 236: 1237–1245 (1987); Ingarham et al., Annual Review of Physiology 52: 773–791 (1990). However, several important cases exist that cannot be readily explained by the action of transcription factors alone. For example, Midgeon, Trends Genet. 10: 230–235 (1994), teaches that X-inactivation involves the inactivation of an allele of a gene that resides on the inactive X-chromosome, while the allele on the active X-chromosome continues to be expressed. In addition, Peterson and Sapienza, Annu. Rev. Genet. 27: 7–31 (1993), describes "parental imprinting", where an allele of a gene that is inherited from one parent is active and the other allele inherited from the other parent is inactive. In both of these cases, both alleles exist in an environment containing the same transcription factors, yet one allele is expressed and the other is silent. Thus, something other than transcription factors must be involved in these phenomena.

Investigators have been probing what type of "epigenetic information" may be involved in this additional control of the expression pattern of the genome. Holliday, Philos. Trans. R. Soc. Lond. B. Biol. Sci. 326: 329–338 (1990) discusses the possible role for DNA methylation in such epigenetic inheritance. DNA contains a set of modifications that is not encoded in the genetic sequence, but is added covalently to DNA using a different enzymatic machinery. These modifications take the form of methylation at the 5 position of cytosine bases in CpG dinucleotides. Numerous studies have suggested that such methylation may well be involved in regulating gene expression, but its precise role has remained elusive. For example, Lock et al., Cell 48: 39–46 (1987), raises questions about whether the timing of hypermethylation and X-inactivation is consistent with a causal role for methylation. Similarly, Bartolomei et al., Genes Dev. 7: 1663–1673 (1993) and Brandeis et al., EMBO J. 12: 3669–3677 (1993), disclose timing/causation questions for the role of methylation in parental imprinting.

Some of the shortcomings of existing studies of the role of DNA methylation in gene expression reside in the tools that are currently available for conducting the studies. Many studies have employed 5-azaC to inhibit DNA methylation. However, 5-azaC is a nucleoside analog that has multiple effects on cellular mechanisms other than DNA methylation, thus making it difficult to interpret data obtained from these studies. Similarly, 5-azadC forms a mechanism based inhibitor upon integration into DNA, but it can cause trapping of DNA methyltransferase (hereinafter, DNA MeTase) molecules on the DNA, resulting in toxicities that may obscure data interpretation.

More recently, Szyf et al., J. Biol. Chem. 267: 12831–12836 (1995), discloses a more promising approach using expression of antisense RNA complementary to the DNA MeTase gene to study the effect of methylation on cancer cells. Szyf and von Hofe, U.S. Pat. No. 5,578,716, discloses the use of antisense oligonucleotides complementary to the DNA MeTase gene to inhibit tumorigenicity. These developments have provided powerful new tools for probing the role of methylation in numerous cellular processes. In addition, they have provided promising new approaches for developing therapeutic compounds that can modulate DNA methylation. The promise of these approaches underscores the importance of developing antisense oligonucleotides complementary to DNA methyltransferase sequences which have optimal activity in inhibiting DNA methyltransferase gene expression. There is, therefore, a need for such optimized antisense oligonucleotides.

BRIEF SUMMARY OF THE INVENTION

The invention provides antisense oligonucleotides complementary to DNA methyltransferase sequences which have optimal activity in inhibiting DNA methyltransferase gene expression. In certain embodiments, the optimized antisense oligonucleotides are characterized by having nucleic acid sequences that provide surprisingly high efficacy. In some of these embodiments, the optimized antisense oligonucleotides according to the invention are further characterized by having distinct chemical modifications which further increase their efficacy. Finally, the invention provides methods for using such antisense oligonucleotides as analytical and diagnostic tools, as potentiators of transgenic plant and animal studies and for gene therapy approaches, and as potential therapeutic agents.

In a first aspect, the invention provides novel optimized antisense oligonucleotides which inhibit the gene expression of DNA MeTase at lower concentration levels of oligonucleotide than previously known oligonucleotides. Such antisense oligonucleotides are complementary to nucleic acid sequences of RNA or double-stranded DNA that encodes DNA MeTase. Preferably, such antisense oligonucleotides contain one or more modified internucleoside linkage and may optionally contain either deoxyribonucleosides, ribonucleosides or 2'-O-substituted ribonucleosides, or any combination thereof. Particularly preferred antisense oligonucleotides according to this aspect of the invention include chimeric oligonucleotides and hybrid oligonucleotides.

In a second aspect, the invention provides a method for investigating the role of DNA MeTase in cellular growth, including the growth of tumor cells. In the method according to this aspect of the invention, the cell type of interest is contacted with an antisense oligonucleotide according to the invention, resulting in inhibition of expression of DNA MeTase in the cell. The antisense oligonucleotides can be administered at different points in the cell cycle, or in conjunction with promoters or inhibitors of cell growth to determine the role of DNA MeTase in the growth of the cell type of interest.

In a third aspect, the invention provides methods for inhibiting tumor growth comprising administering to a mammal, including a human, antisense oligonucleotides according to the invention. In the method according to this aspect of the invention a therapeutically effective amount of an antisense oligonucleotide according to the invention is administered for a therapeutically effective period of time to a mammal, including a human, which has tumor cells present in its body.

DETAILED DESCRIPTION OF THE PREFERRED EMBODIMENTS

The invention relates to modulation of gene expression. In particular, the invention relates to modulation of gene expression of the gene encoding DNA methyltransferase (DNA MeTase), and to modulation of gene expression that is regulated by the enzyme DNA MeTase. The patents and publications identified in this specification are within the knowledge of those skilled in this field and are hereby incorporated by reference in their entirety.

The invention provides antisense oligonucleotides complementary to optimal target DNA MeTase sequences which have optimal activity in inhibiting DNA methyltransferase gene expression. In certain embodiments, the optimized antisense oligonucleotides are characterized by having nucleic acid sequences that provide surprisingly high efficacy. In some of these embodiments, the optimized antisense oligonucleotides according to the invention are further characterized by having distinct chemical modifications which further increase their efficacy. Finally, the invention provides methods for using such antisense oligonucleotides as analytical and diagnostic tools, as potentiators of transgenic plant and animal studies and for gene therapy approaches, and as potential therapeutic agents.

In a first aspect, the invention provides optimal target DNA MeTase nucleotide sequences to be used as preferred targets for the hybridization of optimized antisense oligonucleotides. Intramolecular base pairing plays a pivotal role in the sequestering of sequences, preventing the intramolecular pairing essential to antisense activity. It is believed that duplex formation between antisense oligonucleotides and target sequences is confined to those regions which provide an accessible substructure suitable as a site for nucleation and thus having unpaired bases. Duplex formation will progress from the nucleation site through a 'zippering' process, and stop when this process meets an energy barrier. Such barriers may include for example the ends of stems or sharp turns in the folded RNA. Thus the susceptibility of a target sequence to antisense interaction varies greatly from one part of the sequence to another and is directly related to a particular sequence potential to assemble into an heteroduplex.

Without wishing to be bound to any particular theory, the inventor believes his efforts have led to the identification of DNA MeTase sequences open to duplex formation.

Figure 1:
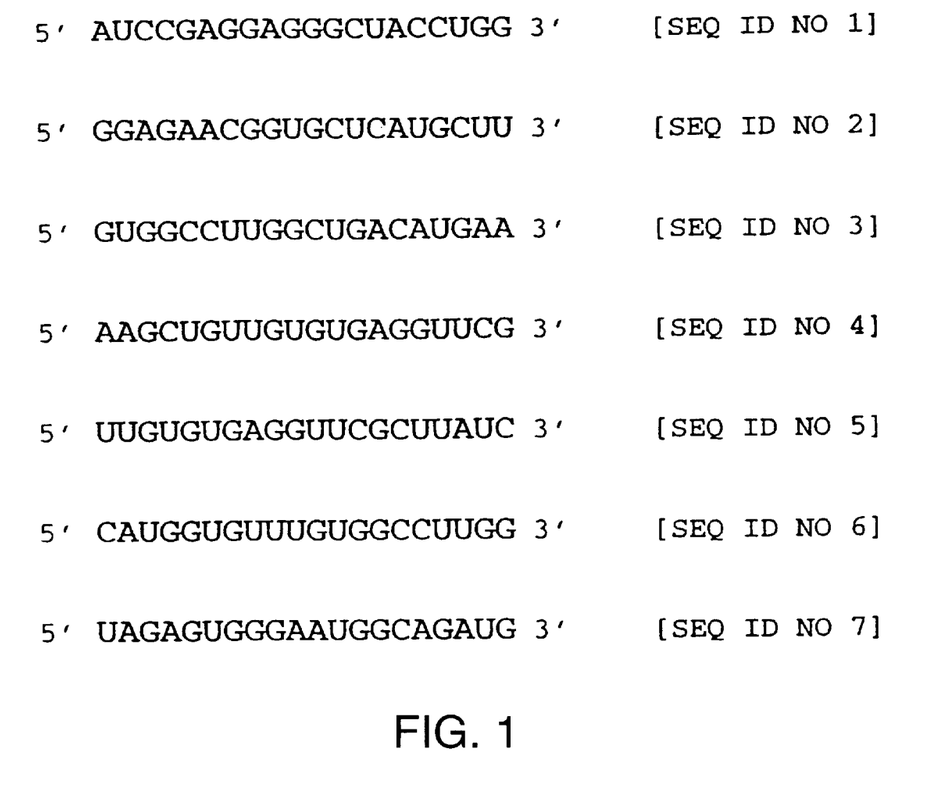
FIG. 1 shows the optimal target DNA MeTase nucleotide sequence for certain preferred oligonucleotides complementary to DNA MeTase RNA, which are set forth in the Sequence Listings as SEQ ID NO 1, SEQ ID NO 2, SEQ ID NO 3, SEQ ID NO 4, SEQ ID NO 5, SEQ ID NO 6, and SEQ ID NO 7.

Examples of optimal target DNA MeTase nucleotide sequences to be used as preferred target for the hybridization of optimized antisense oligonucleotides are shown in FIG. 1. Additional optimal target DNA MeTase nucleotide sequences have sequences which include at least one nucleotide overlap with the target sequences shown in FIG. 1.

The first aspect of the invention also provides novel optimized antisense oligonucleotides which inhibit the gene expression of DNA MeTase. Such antisense oligonucleotides are complementary to optimal target nucleic acid sequences of RNA or double-stranded DNA that encodes DNA MeTase, preferably human DNA MeTase, and are characterized by their ability to inhibit DNA methyltransferase gene expression with an $IC_{50}$ of less than 100 nM, preferably 90 nM or less, more preferably 80 nM or less, still more preferably 70 nM or less, even more preferably 60 nM or less, and most preferably 50 nM or less. Preferably, such inhibition is measured by determining levels of DNA methyltransferase MRNA in A549 human lung cancer cells in vitro. For purposes of the invention, "complementary" means being sufficiently complementary to have the ability to hybridize under physiological conditions to an optimal target DNA MeTase nucleotide sequence which may be a genomic region, a gene, or an RNA transcript thereof. Such hybridization is ordinarily the result of base-specific hydrogen bonding between complementary strands, preferably to form Watson-Crick or Hoogsteen base pairs, although other modes of hydrogen bonding, as well as base stacking can also lead to hybridization. The antisense oligonucleotides of the invention may include one or more modified base capable of hybridization. The term "modified base" as used herein denotes a base other than the five traditional nitrogenous bases: adenine, thymine, guanine, uridine, and cytosine. Such modified bases are capable of hybridization with a complementary traditional base or with a modified base. Hence, for example an antisense oligonucleotide according to the invention may comprise inosine, 5-bromocytosine, or 5-fluorocytosine each of which is capable of hybridizing to a guanine base in the target DNA MeTase sequence. Modified bases according to the invention include without limitation 4-acetylcytidine, 5-(carboxyhydroxylmethyl)uridine, 2'-O-methylcytidine, 5-carboxymethylaminomethyl-2-thioridine, 5-carboxymethylaminomethyluridine, dihydrouridine, 2'-O-methylpseudouridine, beta,D-galactosylqueosine, 2'-O-methylguanosine, inosine, N6-isopentenyladenosine, 1-methyladenosine, 1-methylpseudouridine, 1-methylguanosine, 1-methylinosine, 1,2- dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, beta,D-mannosylqueosine, 5-methoxycarbonylmethyluridine, 5-methoxyuridin, 2-methylthio-N6-isopentenyladenosine, N-((9-beta-D-ribofuranosyl-2-methylthiopurine-6-yl)carbamoyl) threonine, N-((9-beta-D-ribofuranosylpurine-6-yl)N-methyl-carbamoyl)threonine, uridine-5-oxyacetic acid methylester, uridine-5-oxyacetic acid (v), wybutoxosine, pseudouridine, queosine, 2-thiocytidine, 5-methyl-2-thiouridine, 2-thiouridine, 4-thiouridine, 5-methyluridine, N-((9-beta-D-ribofuranosylpurine-6-yl)carbamoyl) threonine, 2'-O-methyl-5-methyluridine, 2'-O-methyluridine, wybutosine, and 3-(3-amino-3-carboxypropyl)uridine, (acp3)u. As a practical matter, such complementarity can be inferred from the observation of specific DNA MeTase gene expression inhibition, as described above. Preferably, such antisense oligonucleotides contain one or more modified internucleoside linkage and may optionally contain either deoxyribonucleosides, ribonucleosides or 2'-O-substituted ribonucleosides, or any combination thereof. Particularly preferred antisense oligonucleotides according to this aspect of the invention include chimeric oligonucleotides and hybrid oligonucleotides.

For purposes of the invention, the term "oligonucleotide" includes polymers of two or more deoxyribonucleosides, ribonucleosides, or 2'-O-substituted ribonucleoside residues, or any combination thereof. Preferably, such oligonucleotides have from about 8 to about 50 nucleoside residues, preferably from about 21 to about 50 nucleoside residues, more preferably from about 21 to about 35 nucleoside residues, and most preferably from about 13 to about 19 nucleoside residues. The nucleoside residues may be coupled to each other by any of the numerous known internucleoside linkages. Such internucleoside linkages include without limitation phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate and sulfone internucleotide linkages. In certain preferred embodiments, these internucleoside linkages may be phosphodiester, phosphotriester, phosphorothioate, or phosphoramidate linkages, or combinations thereof. The term oligonucleotide also encompasses such polymers having chemically modified bases or sugars and/or having additional substituents, including without limitation lipophilic groups, intercalating agents, diamines and adamantane. For purposes of the invention the term "2'-O-substituted" means substitution of the 2' position of the pentose moiety with an -O-lower alkyl group containing 1–6 saturated or unsaturated carbon atoms, or with an -O-aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or such 2' substitution may be with a hydroxy group (to produce a ribonucleoside), an amino or a halo group, but not with a 2'-H group.

Figure 2:
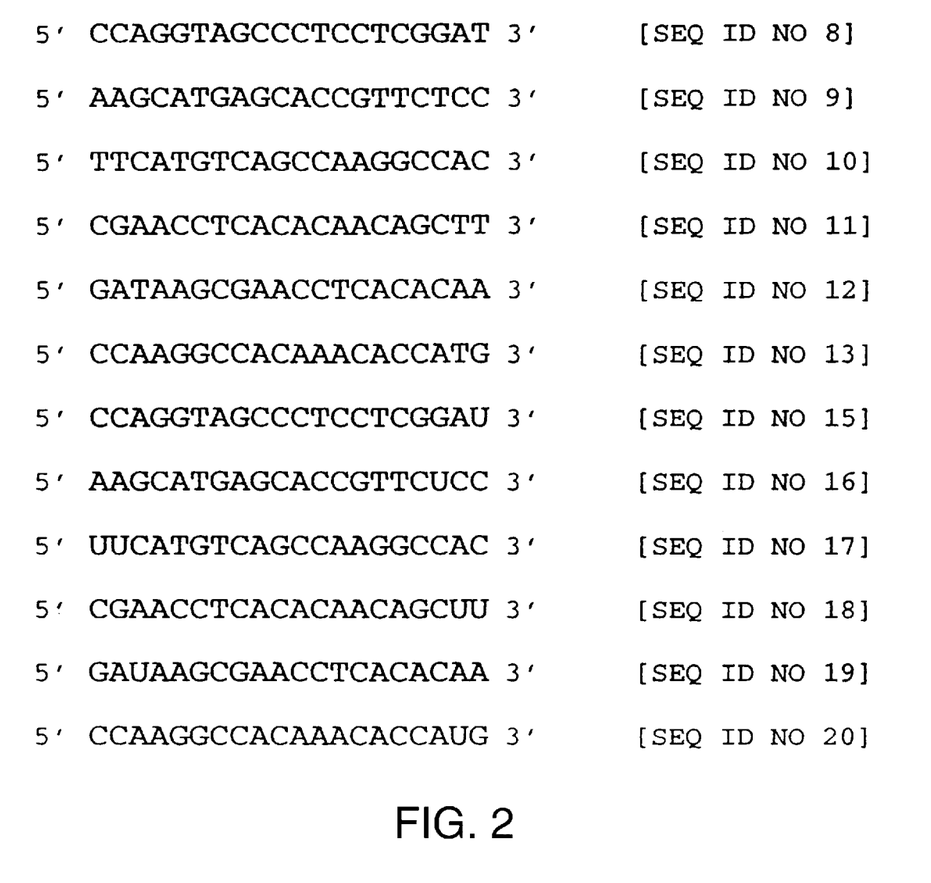
FIG. 2 shows the nucleotide sequence of certain preferred oligonucleotides complementary to DNA MeTase RNA, which are set forth in the Sequence Listings as SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, and SEQ ID NO 20.
Figure 3:
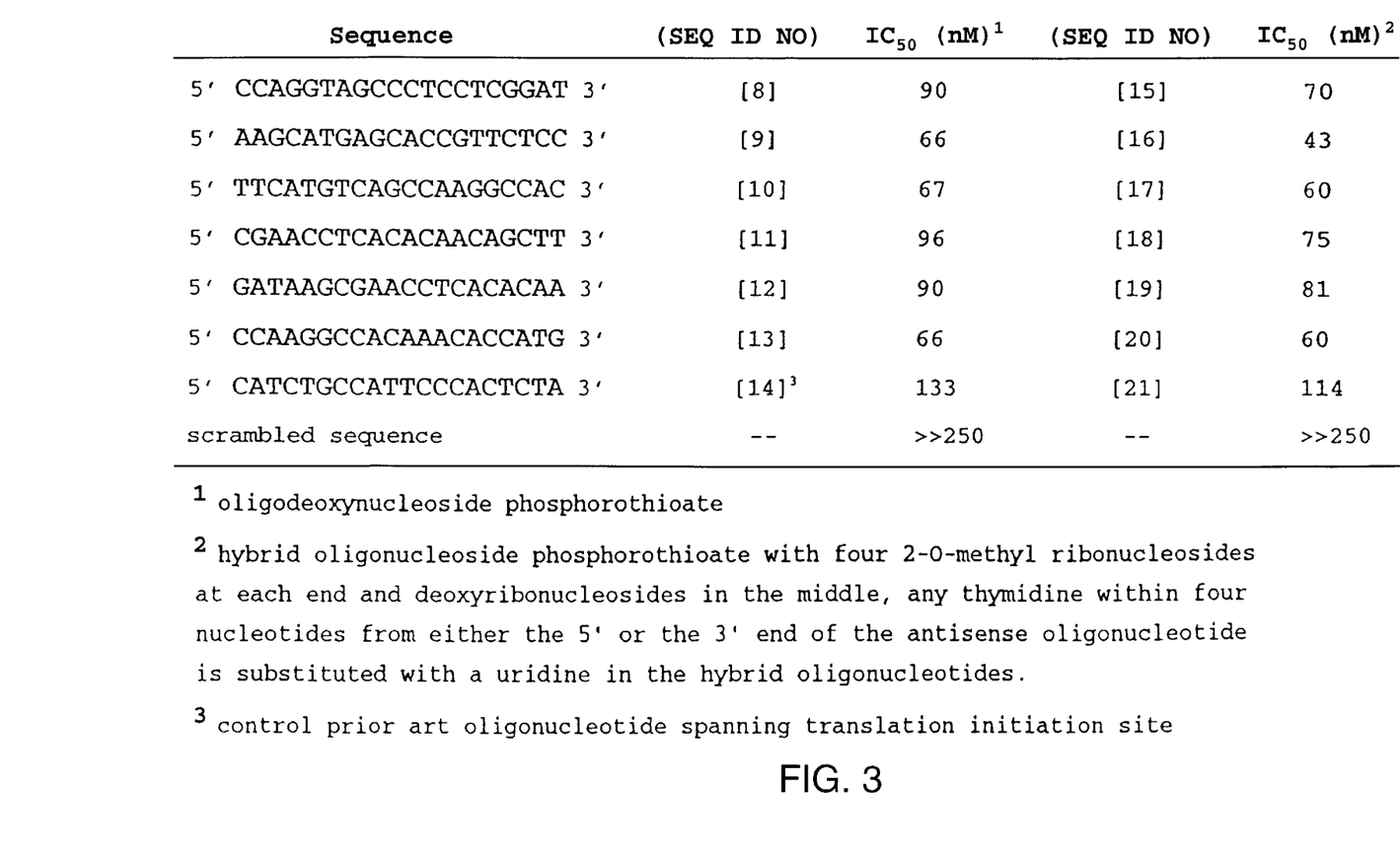
FIG. 3 shows $IC_{50}$ values for various preferred antisense oligonucleotides complementary to DNA MeTase mRNA, as measured by reduction of DNA MeTase mRNA levels in A549 human lung cancer cells in vitro.
Figure 4:
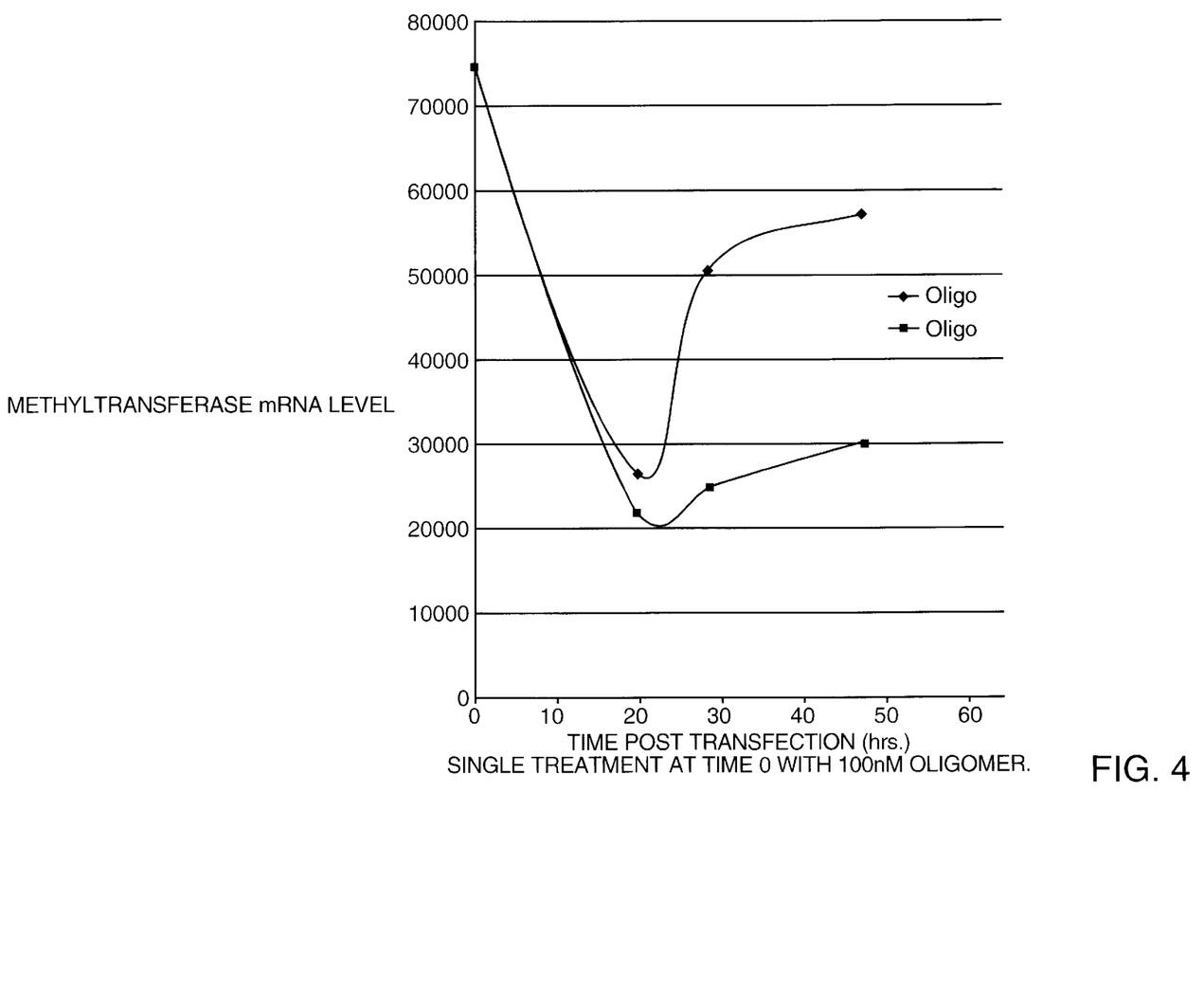
FIG. 4 shows the levels of DNA MeTase mRNA in MDA-231 human breast carcinoma cells treated with the optimized antisense oligonucleotides of the invention (■) as compared to previously known oligonucleotides (♦).

Preferred non-limiting examples of optimized antisense oligonucleotides complementary to RNA or double-stranded DNA encoding DNA MeTase according to the invention are shown in FIG. 2. Additional preferred oligonucleotides have nucleotide sequences of from about 21 to about 35 nucleotides which include the nucleotide sequences shown in FIG. 2. Yet additional preferred oligonucleotides have nucleotide sequences of from about 13 to about 19 nucleotides of the nucleotide sequences shown in FIG. 2.

Particularly preferred antisense oligonucleotides according to this aspect of the invention include chimeric oligonucleotides and hybrid oligonucleotides.

For purposes of the invention, a "chimeric oligonucleotide" refers to an oligonucleotide having more than one type of internucleoside linkage. One preferred embodiment of such a chimeric oligonucleotide is a chimeric oligonucleotide comprising a phosphorothioate, phosphodiester or phosphorodithioate region, preferably comprising from about 2 to about 12 nucleotides, and an alkylphosphonate or alkylphosphonothioate region. Preferably, such chimeric oligonucleotides contain at least three consecutive internucleoside linkages selected from phosphodiester and phosphorothioate linkages, or combinations thereof.

For purposes of the invention, a "hybrid oligonucleotide" refers to an oligonucleotide having more than one type of nucleoside. One preferred embodiment of such a hybrid oligonucleotide comprises a ribonucleotide or 2'-O-substituted ribonucleotide region, preferably comprising from about 2 to about 12 2'-O-substituted nucleotides, and a deoxyribonucleotide region. Preferably, such a hybrid oligonucleotide will contain at least three consecutive deoxyribonucleosides and will also contain ribonucleosides, 2'-O-substituted ribonucleosides, or combinations thereof. In a preferred embodiment, the deoxynucleotide region is flanked on either side by a 2'-O-substituted region. In one particularly preferred embodiment, the 2'-O-substituted regions are 2'-O-methyl regions, most preferably having four 2'-O-methyl nucleosides. In certain preferred embodiments the entire backbone of the oligonucleotide is a phosphorothioate backbone. The superiority of hybrid oligonucleotides according to the invention is demonstrated later in this specification.

The exact nucleotide sequence and chemical structure of an antisense oligonucleotide according to the invention can be varied, so long as the oligonucleotide retains its ability to inhibit DNA MeTase expression at the high levels of efficacy described herein. This is readily determined by testing whether the particular antisense oligonucleotide is active in a DNA MeTase mRNA assay, DNA MeTase enzyme assay, a soft agar growth assay, or an in vivo tumor growth assay, all of which are described in detail in this specification.

Antisense oligonucleotides according to the invention may conveniently be synthesized on a suitable solid support using well known chemical approaches, including H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG). (See, e.g., Pon, Methods in Molec. Biol. 20: 465 (1993)).

Antisense oligonucleotides according to the invention are useful for a variety of purposes. For example, they can be used as "probes" of the physiological function of DNA MeTase by being used to inhibit the activity of DNA methyltransferase in an experimental cell culture or animal system and to evaluate the effect of inhibiting such DNA MeTase activity. This is accomplished by administering to a cell or an animal an antisense oligonucleotide according to the invention and observing any phenotypic effects. In this use, antisense oligonucleotides according to the invention are preferable to traditional "gene knockout" approaches because they are easier to use and can be used to inhibit DNA MeTase activity at selected stages of development or differentiation. Thus, antisense oligonucleotides according to the invention can serve as probes to test the role of DNA methylation in various stages of development.

Finally, antisense oligonucleotides according to the invention are useful in therapeutic approaches to benign and malignant tumors and other human diseases involving suppression of gene expression. The anti-tumor utility of antisense oligonucleotides according to the invention is described in detail elsewhere in this specification. In addition, antisense oligonucleotides according to the invention may be used to activate silenced genes to provide a missing gene function and thus ameliorate disease symptoms. For example, the diseases beta thalassemia and sickle cell anemia are caused by aberrant expression of the adult beta globin gene. Most individuals suffering from these diseases have normal copies of the fetal gene for beta globin. However, the fetal gene is hypermethylated and is silent. Activation of the fetal globin gene could provide the needed globin function, thus ameliorating the disease symptoms.

For therapeutic use, antisense oligonucleotides according to the invention may optionally be formulated with any of the well known pharmaceutically acceptable carriers or diluents. This formulation may further contain one or more DNA MeTase inhibitor and/or one or more additional anti-DNA MeTase antisense oligonucleotide or it may contain any other pharmacologically active agent.

In a second aspect, the invention provides a method for investigating the role of DNA MeTase in cellular growth, including the growth of tumor cells. In the method according to this aspect of the invention, the cell type of interest is contacted with an antisense oligonucleotide according to the invention, resulting in inhibition of expression of DNA MeTase in the cell. The antisense oligonucleotides can be administered at different points in the cell cycle, or in conjunction with promoters or inhibitors of cell growth to determine the role of DNA MeTase in the growth of the cell type of interest.

In a third aspect, the invention provides methods for inhibiting tumor growth comprising administering to a mammal, including a human, antisense oligonucleotides according to the invention. In the method according to this aspect of the invention a therapeutically effective amount of an antisense oligonucleotide according to the invention is administered for a therapeutically effective period of time to a mammal, including a human, which has tumor cells present in its body.

As used herein the term "tumor growth" is used to refer to the growth of a tumor cell. A "tumor cell" is a neoplastic cell. A tumor cell may be benign, i.e. one that does not form metastases and does not invade and destroy adjacent normal tissue, or malignant, i.e. one that invades surrounding tissues, is capable of producing metastases, may recur after attempted removal, and is likely to cause death of the host.

The terms "therapeutically effective amount" and "therapeutically effective period of time" are used to denote known treatments at dosages and for periods of time effective to reduce tumor cell growth. Preferably, such administration should be parenteral, oral, sublingual, transdermal, topical, intranasal or intrarectal. When administered systemically, the therapeutic composition is preferably administered at a sufficient dosage to attain a blood level of antisense oligonucleotide from about 0.01 uM to about 10 uM. For localized administration, much lower concentrations than this may be effective, and much higher concentrations may be tolerated. Preferably, a total dosage of DNA MeTase inhibitor will range from about 0.1 mg oligonucleotide per patient per day to about 200 mg oligonucleotide per kg body weight per day.

According to another embodiment, one or more of the oligonucleotides of the invention may be administered to an animal. This aspect of the invention provides methods for inhibiting tumor growth comprising administering to an animal, including a human, more than one antisense oligonucleotide according to the invention either sequentially or simultaneously in a therapeutically effective amount and for a therapeutically effective period of time.

The following examples are intended to further illustrate certain preferred embodiments of the invention and are not limiting in nature.

EXAMPLE 1

Inhibition of DNA MeTase Expression As Measured in Nuclear Extracts Prepared from Human or Murine Cells Nuclear extracts are prepared from $1 \times 10^8$ mid-log phase human H446 cells or mouse Y1 cells which have been grown under standard cell culture conditions. Cells were treated with medium supplemented with 1 mg/ml of an antisense oligonucleotide complementary to a sequence of the DNA MeTase RNA transcript or a randomer (negative control) oligonucleotide. The cells are harvested and washed twice with phosphate buffered saline (PBS), then the cell pellet is resuspended in 0.5 ml Buffer A (10 mM Tris pH 8.0, 1.5 mM $MgCl_2$, 5 mM $KCl_2$, 0.5 mM DTT, 0.5 mM PMSF and 0.5% Nonidet P40) to separate the nuclei from other cell components. The nuclei are pelleted by centrifugation in an Eppendorf microfuge at 2,000 RPM for 15 min at 4° C. The nuclei are washed once in Buffer A and re-pelleted, then resuspended in 0.5 ml Buffer B (20 mM Tris pH 8.0, 0.25% glycerol, 1.5 mM $MgCl_2$, 0.5 mM PMSF, 0.2 mM EDTA 0.5 mM DTT and 0.4 mM NaCl). The resuspended nuclei are incubated on ice for 15 minutes then spun at 15,000 RPM to pellet nuclear debris. The nuclear extract in the supernatant is separated from the pellet and used for assays for DNA MeTase activity. For each assay, carried out in triplicate, 3 ug of nuclear extract is used in a reaction mixture containing 0.1 ug of a synthetic 33-base pair hemimethylated DNA molecule substrate with 0.5 uCi S-[methyl- $^3$H] adenosyl-L-methionine (78.9 Ci/mmol) as the methyl donor in a buffer containing 20 mM Tris-HCl (pH 7.4), 10 mM EDTA, 25% glycerol, 0.2 mM PMSF, and 20 mM 2-mercaptoethanol. The reaction mixture is incubated for 1 hour at 37° C. to measure the initial rate of the DNA MeTase. The reaction is stopped by adding 10% TCA to precipitate the DNA, then the samples are incubated at 4° C. for 1 hour and the TCA precipitates are washed through GFC filters (Fischer, Hampton, N.H.). Controls are DNA incubated in the reaction mixture in the absence of nuclear extract, and nuclear extract incubated in the reaction mixture in the absence of DNA. The filters are laid in scintillation vials containing 5 ml of scintillation cocktail and tritiated methyl groups incorporated into the DNA are counted in a -scintillation counter according to standard methods. To measure inhibition of DNA MeTase expression, the specific activity of the nuclear extract from oligonucleotide-treated cells is compared with the specific activity of the extract from untreated cells. Treatment of cells with antisense oligonucleotides of the invention results in reduction in DNA MeTase activity in the nuclear extract.

EXAMPLE 2
Inhibition of DNA MeTase Expression As Measured by mRNA in A549 Cells A549 cells growing in culture were treated with DNA Methyltransferase antisense oligonucleotides in the presence of 6.25 ug/ml of lipofectin (GIBCO BRL) in Optimem serum free medium (GIBCO) for 4 hrs, cells were then washed once with PBS and then cells were returned to DMEM medium (GIBCO) containing 10% fetal calf serum. 24 hrs after addition of the oligonucleotide total cellular RNA was isolated from A549 cells, run on denaturing agarose gel, transferred to nylon membrane (Northern blot). Membranes were then hybridized with a radiolabeled DNA Methyltransferase specific probe, washed and exposed to X-ray film. The level of DNA Methyltransferase expression in control and treated cells was determined by quantification of DNA Methyltransferase signal. Membranes were then stripped and rehybridized with a probe specific for G3PDH (Glyceraldehyde 3-phosphate, dehydrogenase) as a non-antisense target gene to control for non specific effects and for loading of the total RNA. DNA methyltransferase levels were determined by dividing the signal obtained for the DNA Methyltransferase by that obtained for G3PDH.

EXAMPLE 3
Analysis of Cellular DNA Methylation in Cells Treated with Antisense Oligonucleotides Nuclear extracts are prepared from randomer oligonucleotide-treated cells and from antisense oligonucleotide-treated cells (1 uM oligonucleotide) as described in Example 1. The DNA pellet is resuspended in 0.5 ml DNA extraction buffer (0.15 M NaCl, 1% SDS, 20 mM Tris-HCl pH 8.0, 5 mM EDTA), 100 ug Proteinase K is added, and the suspension is incubated at 50° C. for 16 hours. The DNA is extracted in phenol-chloroform by adding 0.25 ml phenol and 0.25 ml chloroform. The suspension is mixed and the organic and aqueous phases are separated by centrifugation in a microfuge for 10 minutes at 15,000 RPM. One ml absolute ethanol is added to the aqueous phase and the DNA is precipitated by centrifugation in a microfuge for 15 minutes at 15,000 RPM. The DNA pellet is washed in 70% ethanol and re-pelleted by centrifugation. The DNA is resuspended in 100 ul 20 mM Tris-HCl pH 8.0, 1 mM EDTA.

Two ug DNA are incubated at 37° C. for 15 minutes with 0.1 unit of DNase, 2.5 ul $^{32}$P-dGTP (3000 Ci/mmol, Amersham, (Cleveland, Ohio) and then 2 units Kornberg DNA Polymerase (Boehringer Mannheim, Mannheim, Germany) are added and the reaction mixture is incubated for an additional 25 minutes at 30° C. Fifty ul $H_2O$ are then added and nonincorporated radioactivity is removed by spinning through a Microspin S-300 HR column (Pharmacia, Piscataway, N.J.). Labelled DNA (20 ul) is digested with 70 ug micrococcal nuclease (Pharmacia, Piscataway, N.J.) in the manufacturer's recommended buffer for 10 hours at 37° C. Equal amounts of radioactivity are loaded onto TLC phosphocellulose plates (Merck, Darmstadt, Germany) and the 3' mononucleotides are separated by chromatography in one direction, in 66:33:1 isobutyric acid/$H_2O$/$NH_4OH$. The chromatograms are exposed to XAR film (Eastman Kodak, Rochester, N.Y.) and the autoradiograms are scanned by laser densitometry (Scanalytics, CSPI, Billerica, Mass.). Spots corresponding to cytosine and 5-methylcytosine are quantified and the percentage of non-methylated CG dinucleotides is determined. The results are expected to demonstrate an overall reduction in the percentage of non-methylated CG dinucleotides in antisense oligonucleotide-treated cells, relative to randomer-treated cells.

To assess demethylation of specific genes, a procedure is carried out as generally described in J. Biol. Chem. 270: 12690–12696 (1995). Briefly, the genomic DNA (10 ug) is extracted and subjected to digestion by 25 units HindIII, followed by digestion by either 25 units MspI (CG methylation insensitive) or 25 units HpaII (CG methylation sensitive) for 8 hours at 37° C. The digested DNA is separated on a 1.5% agarose gel and subjected to Southern blotting and hybridization with specific probes. The results are expected to show that genes which are ordinarily heavily methylated in the test cells become undermethylated, whereas the methylation levels for genes which are not ordinarily heavily methylated in the test cells are not significantly affected.

EXAMPLE 4
Inhibition of In Vitro Tumor Growth By Antisense Oligonucleotides

Y1 or H446 cells are plated on a 6 well plate at a density of 80,000 cells/well. Antisense oligonucleotide phosphorothioates complementary to a DNA MeTase noncoding region (about 0.5 to 20 uM) are added to the cells. The cells are similarly treated daily for 7 days. Then, the cells are harvested and 3,000 live cells are plated in soft agar, for example, as described in Freedman and Shin, Cell 3: 355–359 (1974). Two weeks after plating, the number of colonies formed in soft agar are scored by visual examination. In the case of active antisense oligonucleotides, a dose-dependent reduction in the number of colonies is observed.

EXAMPLE 5
Inhibition of Tumor Growth In Vivo

Ten to twelve week old female BALB/c nude mice (Taconic Labs, Great Barrington, N.Y.) were injected subcutaneously in the flank area with 2×10$^6$ preconditioned A549 human lung carcinoma cells or Colo205 human colon cancer cells. Preconditioning of these cells was done by a minimum of three consecutive tumor transplantations in the same strain of nude mice. Subsequently, tumor fragments of approximately 25 mgs were excised and implanted subcutaneously in mice, in the left flank area under Forene anesthesia (Abbott Labs., Geneva, Switzerland). When the tumors reached a mean volume of 100 mm$^3$, the mice were treated intravenously, by daily bolus infusion into the tail vein, with oligonucleotide saline preparations containing 2 mg/Kg of oligonucleotide according to the present invention. The optimal final concentration of the oligonucleotide is established by dose response experiments according to standard protocols. Tumor volume was calculated according to standard methods every second day post infusion. (e.g., Meyer et al. Int. J. Cancer 43:851–856 (1989)). Treatment with the oligonucleotides of the invention caused a significant reduction in tumor weight and volume relative to controls treated with randomized or reverse antisense sequence (data not shown). In addition, the activity of DNA MeTase enzyme was measured and found to be significantly reduced relative to randomer treated controls. These results show that the oligonucleotides according to the invention are capable of inhibiting MeTase enzymatic activity and tumor growth.

What is claimed is:

1. An antisense oligonucleotide complementary to nucleic acid sequences of RNA or double-stranded DNA that encodes DNA MeTase and which inhibits DNA methyltransferase gene expression, wherein the oligonucleotide is selected from the group consisting of SEQ ID NO: 8, SEQ ID NO: 9, SEQ ID NO: 10, and SEQ ID NO: 13.

2. The oligonucleotide according to claim 1, wherein the oligonucleotide is a chimeric oligonucleotide comprising a phosphorothioate, phosphodiester or phosphorodithioate region and an alkylphosphonate or alkylphosphonothioate region.

3. The oligonucleotide according to claim 1, wherein the oligonucleotide comprises a ribonucleotide or 2'-O-substituted ribonucleotide region and a deoxyribonucleotide region.

4. A method for inhibiting tumor growth in a human comprising administering to the human, which has at least one tumor cell present in its body, a therapeutically effective amount of an antisense oligonucleotide according to claim 1 for a therapeutically effective period of time.

5. The method of claim 1, wherein the human is administered a therapeutically effective amount of more than one antisense oligonucleotide according to claim 1 for a therapeutically effective period of time.

* * * * *

UNITED STATES PATENT AND TRADEMARK OFFICE
CERTIFICATE OF CORRECTION

PATENT NO : 6,066,625
DATED : May 23, 2000
INVENTOR(S): Robert A. MacLeod It is certified that error appears in the above-identified patent and that said Letters Patent are hereby corrected as shown below:

```
In claim 5, line 30, after "claim", "1" should be changed
to --4--.
```

Signed and Sealed this

Third Day of April, 2001

*Attest:*

NICHOLAS P. GODICI

*Attesting Officer*  *Acting Director of the United States Patent and Trademark Office*